United States Patent [19]

Otte et al.

[11] Patent Number: 4,720,597

[45] Date of Patent: Jan. 19, 1988

[54] PROCESS FOR THE PRODUCTION OF HYDROXYMETHYLCYCLOPROPANE (CYCLOPROPYLMETHANOL)

[75] Inventors: Werner Otte, Dortsen; Rudolf Nehring, Marl, both of Fed. Rep. of Germany

[73] Assignee: Huels Aktiengesellschaft, Marl, Fed. Rep. of Germany

[21] Appl. No.: 922,914

[22] Filed: Oct. 24, 1986

[30] Foreign Application Priority Data

Oct. 26, 1985 [DE] Fed. Rep. of Germany ....... 3538132

[51] Int. Cl.$^4$ ............................................. C07C 29/132
[52] U.S. Cl. ................................................. 568/814
[58] Field of Search ............... 568/840, 822, 839, 834, 568/814

[56] References Cited

U.S. PATENT DOCUMENTS

| | | | |
|---|---|---|---|
| 3,959,324 | 5/1976 | Peterson et al. | 560/44 |
| 3,960,907 | 6/1976 | Henricks et al. | 560/124 |
| 3,998,889 | 12/1976 | Peterson et al. | 560/44 |
| 4,036,877 | 7/1977 | Petro et al. | 568/490 |
| 4,065,480 | 12/1977 | Peterson et al. | 560/44 |
| 4,085,273 | 4/1978 | Peterson et al. | 560/124 |
| 4,211,727 | 7/1980 | Entwisle et al. | 568/490 |

OTHER PUBLICATIONS

Corey, "J. Amer. Chem. Soc." vol. 82, pp. 2645–2646.
Beilsteins Handbuch IV6 p. 4 (1923).
*Organic Chemistry*, Morrison et al., 3rd Ed., Allyn & Bacon (1973).

*Primary Examiner*—Werren B. Lone
*Attorney, Agent, or Firm*—Millen & White

[57] ABSTRACT

For the selective production of hydroxymethylcyclopropane, cyclopropanecarboxylic acid esters are hydrogenated in the presence of a Zn chromite catalyst in the sump phase or trickling phase under a hydrogen pressure of 200–320 bar and at temperatures of 200°–350° C. Preferably, cyclopropanecarboxylic acid esters are used, the alcohol component of which contains 1–10, especially 1–8 carbon atoms.

17 Claims, No Drawings

PROCESS FOR THE PRODUCTION OF HYDROXYMETHYLCYCLOPROPANE (CYCLOPROPYLMETHANOL)

BACKGROUND OF THE INVENTION

The invention relates to a process for the selective production of hydroxymethylcyclopropane from esters of cyclopropanecarboxylic acid in the presence of commercially available zinc chromite catalysts. Hydroxymethylcyclopropane is a known chemical utilized as an intermediate product for the synthesis of, for example, bactericides, fungicides, herbicides and insecticides.

Preparation of these products, for example, pesticides; bactericides, fungicides, herbicides and insecticides, is disclosed for example in the U.S. Pat. No. 3,959,324; U.S. Pat. No. 3,998,889; U.S. Pat. No. 4,065,480.

In accordance with conventional methods, hydroxymethylcyclopropane is obtained from cyclopropanecarboxylic acid in the presence of lithium aluminum hydride (Beilstein E IV 6: 4) or by reactions of cyclopropanecarboxylic acid with organometallic compounds in the presence of electrophilic compounds. (U.S. Pat. No. 4,085,273; U.S. Pat. No. 4,054,480; U.S. Pat. No. 3,998,889; U.S. Pat. No. 3,959,324) or by anodic oxidation of cyclobutanecarboxylic acid (*J. Am. Chem. Soc.* 82: 2645 to 2646 [1960]).

These processes are rather expensive and require several complicated and costly chemicals, furthermore, the yields are only moderate.

SUMMARY OF THE INVENTION

It is therefore an object of the invention to provide an economical process for the production of hydroxymethylcyclopropane which eliminates the use of expensive chemicals that are not easy to handle, and also results in a high yield of hydroxymethylcyclopropane.

This objective has been attained by the provision of a process comprising hydrogenating cyclopropanecarboxylic acid esters in the liquid phase in the presence of a zinc chromite catalyst. Liquid phase hydrogenation includes reactions in the bottoms or "sump phase", as well as reactions wherein the starting materials are partially in liquid phase and are trickled down from the top of the reactor, i.e., in the "trickling phase".

This invention is directed to the use of zinc chromite as a catalyst. This catalyst is described by Zymalkowsky "Katalycische Hydrierungen im org. chem. Praktikum", Enke Verlag Stuttgart, Neue Folge 61 (1965), pages 32-34.

It has been found surprisingly that with the process of this invention, hydroxymethylcyclopropane is obtained in an almost quantitative yield with approximately complete conversion, i.e., the cyclopropane, ring-containing product of the reaction consists essentially of the hydroxymethyl compound.

The yield of hydroxy-methylcyclopropane is nearly 97% of theory based on starting material. Other derivates of cyclopropane have not been determined.

The process of this invention is preferably performed at a temperature of about 200°-350° C., preferably about 250°-300° C., more preferably 240°-300° C. Furthermore, the hydrogen pressure used in the process of this invention is preferably above 200 bar, more preferably 200 to 320 bar, most preferably 240-300 bar.

Especially suitable as starting materials are cyclopropanecarboxylic acid esters, the alcohol component of which exhibits 1-10, preferably 1-8 carbon atoms. Mixtures of such ester may be used.

Esters of $C_1$-$C_8$-alcohols are preferably used (see Examples 1-3). The yield is between 95.8 and 97% of theory based on starting material. A relationship between the length of the chain of the alcohol component and the yield of hydroxymethylcyclopropane has not been found.

Preferably, the process of this invention is conducted without a solvent, but a solvent may be used in the process.

In the process of this invention, a commercially available zinc chromite catalyst (for example BASF S5-10) is used. Suitable zinc chromite catalysts generally contain 40-80% by weight of ZnO and 10-40% by weight of $Cr_2O_3$. The CuCr catalysts usually employed for the hydrogenation of carboxylic acid esters enable almost complete conversion predominantly to n-butanol, with only a small amount of hydroxymethylcyclopropane.

The process of this invention can be performed discontinuously as well as continuously in a conventional manner, for example in a stirred autoclave or in a reaction tube. The devices required for hydrogenation are fully conventional. The process of this invention can be carried out in the sump phase or trickling phase.

In the trickling phase, the starting material and hydrogen are fed by direct current to the top of a vertically arranged reactor and passed over the catalyst. As a consequence of the pressure and temperature maintained during the reaction, a major part of the starting material is in the gas phase, the remainder is in the liquid phase and trickles from top to bottom through the reactor. In the sump phase the process is carried out in the liquid phase.

In the case of a discontinuously performed process, the operation takes place customarily in the sump phase in an autoclave in the presence of a pulverulent catalyst.

The process according to this invention can be performed especially advantageously in a continuous fashion. This is done by conducting the liquid starting material over the catalyst present in the reaction tube and arranged in lumps, for example in accordance with the trickling phase principle, while the hydrogen is passed cocurrently or countercurrently through the reaction tube. Advantageously, the excess hydrogen is recirculated.

The special advantages of the process of this invention reside in the simplicity of its conductance, and its economy.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated. "Nl" denotes "normal liters", i.e., liters under normal conditions (0° C., 1 atm absolute).

Furthermore, where the starting materials in the claims state specific components, it is intended to include sources of these components as well, e.g., combinations of materials that would form zinc chromite in situ.

EXAMPLE 1

Per hour, 100 ml of cyclopropanecarboxylic acid methyl ester and 400 Nl of hydrogen are conducted through a reaction tube, filled with 400 ml of Zn chromite catalyst. The temperature is 270° C., and the pressure is 300 bar. The hydrogenated product contains the following:
  Forerunnings: 0.2%
  n-Butanol: 0.5%
  Hydroxymethylcyclopropane: 66.6%
  Methanol: 30.5%
  Cyclopropanecarboxylic ester: 0.2%
  Total Intermediate Runnings: 1.5%
  Remainder: 0.5%

EXAMPLE 2

The process is conducted as in Example 1, but using the n-butyl ester of cyclopropanecarboxylic acid. The hydrogenated product is composed of the following:
  Forerunnings: 0.3%
  n-Butanol: 50.3%
  Hydroxymethylcyclopropane: 47.4%
  Ester: 0.1%
  Total Intermediate Runnings: 1.3%
  Remainder: 0.6%

EXAMPLE 3

The process is performed as in Example 1, but with the use of the 2-ethylhexyl ester of cyclopropanecarboxylic acid. The hdyrogenated product has the following composition:
  Forerunnings: 0.2%
  n-Butanol: 0.4%
  Hydroxymethylcyclopropane: 34.1%
  2-Ethylhexanol: 64.0%
  Ester: 0.2%
  Total Intermediate Runnings: 0.9%
  Remainder: 0.2%

EXAMPLE 4

The process of Example 3 is repeated, but the temperature is increased to 300° C. The hydrogenated product has the following composition:
  Forerunnings: 0.4%
  n-Butanol: 1.9%
  Hydroxymethylcyclopropane: 30.5%
  2-Ethylhexanol: 64.3%
  Ester: <0.1%
  Total Intermediate Runnings: 2.4%
  Remainder: 0.5%

EXAMPLE 5

The process of Example 3 is repeated, but the temperature is lowered to 250° C. The hydrogenated product shows the following composition:
  Forerunnings: 0.1%
  n-Butanol: 0.3%
  Hydroxymethylcyclopropane: 32.4%
  2-Ethylhexanol: 62.3%
  Ester: 4.1%
  Total Intermediate Runnings: 0.6%
  Remainder: 0.2%

COMPARATIVE EXAMPLE

The process is performed as set forth in Example 1, but using, in place of a ZnCr catalyst, a CuCr catalyst (HARSHAW 1107), and lowering the reaction temperature to 210° C. The hydrogenated product shows the following composition:
  Forerunnings: 2.8%
  Methanol: 30.7%
  n-Butanol: 59.3%
  Hydroxymethylcyclopropane: 4.9%
  Ester: 0.2%
  Intermediate Runnings: 1.2%
  Remainder: 0.9%

The concentrations indicated in the examples are determined by gas chromatography and relate to percent per unit area.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the selective production of hydroxymethylcyclopropane, said process comprising hydrogenating a cyclopropanecarboxylic acid ester in the liquid phase in the presence of a catalytic amount of zinc chromite, at a sufficiently high temperature and at a sufficiently high pressure so as to produce hydroxymethylcyclopropane.

2. A process according to claim 1, wherein the reaction is conducted at a hydrogen pressure of 200-320 bar.

3. A process according to claim 1, wherein the reaction is conducted at a hydrogen pressure of 240-300 bar.

4. A process according to claim 1, wherein the reaction is conducted at a temperature of 200°-350° C.

5. A process according to claim 1, wherein the reaction is conducted at a temperature of 200°-300° C.

6. A process according to claim 1, wherein the reaction is conducted at a temperature of 240°-300° C.

7. A process according to claim 1, wherein the alcohol component of the cyclopropanecarboxylic acid ester contains 1-10 carbon atoms.

8. A process according to claim 1, wherein the alcohol component of the cyclopropanecarboxylic acid ester contains 1-8 carbon atoms.

9. A process according to claim 1, wherein cyclopropanecarboxylic acid methyl ester is hydrogenated.

10. A process according to claim 1, wherein cyclopropanecarboxylic acid n-butyl ester is hydrogenated.

11. A process according to claim 1, wherein cyclopropanecarboxylic acid 2-ethylhexyl ester is hydrogenated.

12. A process according to claim 1, wherein the hydrogenation reaction is performed discontinuously.

13. A process according to claim 1, wherein the hydrogenation reaction is performed continuously.

14. A process according to claim 13, wherein the reaction is performed in a reactor wherein the cyclopropanecarboxylic acid ester is added as a liquid at the top of the reactor and trickles downward.

15. A process according to claim 14, wherein hydrogen is passed cocurrently through the reaction.

16. A process according to claim 14, wherein hydrogen is passed countercurrently through the reaction.

17. A process according to claim 1, wherein the resultant cyclopropane ring-containing reactor product consists essentially of hydroxymethylcyclopropane.

* * * * *